US005789010A

United States Patent [19]
Behan et al.

[11] Patent Number: 5,789,010
[45] Date of Patent: *Aug. 4, 1998

[54] MALODORS REDUCTION

[75] Inventors: John Martin Behan; Keith Douglas Perring; Brian James Willis, all of Kent, England

[73] Assignee: Unilever Patent Holdings B.V., Rotterdam, Netherlands

[*] Notice: The portion of the term of this patent subsequent to Apr. 20, 2010, has been disclaimed.

[21] Appl. No.: 980,156

[22] Filed: Nov. 23, 1992

Related U.S. Application Data

[62] Division of Ser. No. 782,796, Oct. 25, 1991, Pat. No. 5,204,023, which is a continuation of Ser. No. 507,833, Apr. 12, 1990, abandoned.

[30] Foreign Application Priority Data

Apr. 12, 1989 [GB] United Kingdom ............... 8908199

[51] Int. Cl.$^6$ ............................. C11D 13/00; C11B 1/00; A23D 9/00
[52] U.S. Cl. .................. 426/534; 426/650; 426/601; 426/610; 426/613; 512/1; 512/2; 252/367; 252/368
[58] Field of Search ........................ 426/534, 650, 426/601, 610, 613; 512/1, 2; 252/367–368

[56] References Cited

U.S. PATENT DOCUMENTS

| | | | |
|---|---|---|---|
| 3,725,208 | 4/1973 | Maczawa et al. | 203/8 |
| 5,204,023 | 4/1993 | Behan et al. | 426/534 X |

FOREIGN PATENT DOCUMENTS

| | | |
|---|---|---|
| 0175871 | 4/1986 | European Pat. Off. . |
| 0247946 | 12/1987 | European Pat. Off. . |
| 555146 | 7/1957 | France . |
| 2005896 | 12/1969 | France . |
| 1795617 | 8/1972 | Germany . |
| 1068712 | 5/1967 | United Kingdom . |
| 1596752 | 8/1981 | United Kingdom . |
| 1596753 | 8/1981 | United Kingdom . |

*Primary Examiner*—Cynthia L. Nessler
*Attorney, Agent, or Firm*—Pillsbury Madison & Sutro LLP

[57] ABSTRACT

The invention concerns a method of reducing the organoleptic effect of undesirable aldehydic components in a triglyceride or derivative thereof by addition of a reaction product of an amine and an organoleptically acceptable aldehyde. The triglyceride may be a food or food component such as an edible fat or a surface active agent such as a detergent. The reaction product may be incorporated in the perfume or flavour to be added to the triglyceride or derivative thereof without distorting their organoleptic effect.

1 Claim, No Drawings

MALODORS REDUCTION

This patent application is a divisional of application No. 07/782,796, filed Oct. 25, 1991 and which issued as U.S. Pat. No. 5,204,023 on Apr. 20, 1993, which is a continuation of application No. 07/507,833, filed Apr. 12, 1990, now abandoned.

FIELD OF THE INVENTION

This invention relates to a method for removing or reducing unpleasant malodors or off-flavours arising from the presence of aldehydic materials in fats, oils and related products.

BACKGROUND TO THE INVENTION

Fats and oils are complex water insoluble substances derived from animal or vegetable sources and comprised of a large number of organic materials. The major components are glyceryl esters of fatty acids, particularly triglyceryl esters derived from lauric, myristic, palmitic, stearic, erucic, oleic, linoleic and linolenic acids. Traditionally, oils are distinguished from fats only in that they are liquid at room temperature, and for convenience, the term 'fats' as used hereafter will be assumed to refer equally to oils.

Commercial exploitation of fats is extensive. Millions of tonnes of fats are directly used per annum in edible products, the most important of which are butter, margarine, lard, shortening, mayonnaise, salad oil and cooking oil. Large quantities of fat are also used directly in non-food products, for example, in grease and lubricants, in cosmetics, and in paints and varnishes (as 'drying oils'). In addition, fats are valuable raw materials in the chemicals industry as major sources of fatty acids and their derivatives, among which particular mention should be made of salts, esters, alcohols, amides and other nitrogen derivatives. Manufactured products which commonly incorporate fatty acids or fatty acid derivatives are soaps, plasticisers, polymers, rubber tyres, cosmetics and alkyd resins.

A large proportion of the non-food consumption of fats is accounted for by the production of surface active agents for use as detergents, cleansers and emulsifiers. Among the most important surface active agents are soaps, ie salts of fatty acids with sodium, potassium or other metal cations, or with non-metallic cations such as those containing a quadrivalent nitrogen atom. Many other classes of fatty acid-based surface active agents eg. fat derived surfactants including secondary alkane suphonates, alcohol sulphates, ethoxylated fatty alcohol sulphates, mono and dialkanolamides and alkanolamide sulphates, fatty alcohol ethoxylates, polyethoxylated fatty acid esters, ethoxylated alkanolamides; cationics (particularly quarternary ammonium compounds); amine oxides, ethoxylated derivatives of amine oxides, and amphoterics and sorbitan esters are known and utilised in the synthetic detergent industry.

Glyceride derived emulsifiers are used in the food industry and the present invention relates to them also. Examples are mono-/di-glycerides and their esters with lactic acid, citric acid, acetic anhydride and diacetyltartaric acid; stearoyl lactylates; fatty acid esters of sucrose, sorbitol, propylene glycol and polyglycerol; poly (fatty acid) esters of polyglycerol.

A problem feature of many of the above mentioned products arises from the occurrence in fats of materials which are odoriferous and which have the potential to adversely affect products' odour properties, and also, by extension to the edible products area, the perception of taste, since this is influenced by both flavour and odour. The magnitude of the problem is generally difficult to gauge since the occurrence of the odoriferous materials is dependent on many factors such as type of constituent fats, geographical source, chemical and thermal history of the fats, storage conditions, age of product, and presence or absence of preservatives and anti-oxidants. Often, several of these factors may vary simultaneously with the result that odour problems may occur spasmodically and be difficult to rationalise. Furthermore, it is clear the intrinsic odour characteristics of the product itself, and its intended use, will also have a bearing on the required quality of the incorporated fat.

An example of a malodorous material is the unsaturated aldehyde 2,4-decadienal which gives a distinctive green note at sub ppb levels. This aldehyde has been detected in the headspace above deteriorated soya bean oil. Other malodour aldehydes are known to be present in fat derived materials, e.g. 2,4-dodecadienal.

General description of the invention

It is the aim of the present invention to reduce such problems by the addition of flavours or fragrances which are robust in action, and are unusual in that they possess not only perfumery or flavour components capable of eliciting pleasant sensory responses but in addition they incorporate chemically reactive components which are compatible with fragrances/flavours and whose presence may reduce the concentration of the aldehydic materials often associated with rancidity.

The invention provides a method of reducing the organoleptic effect of an undesirable aldehydic component in a triglyceride or derivative thereof by addition of the product of an amine with an organoleptically acceptable aldehyde. The product may be incorporated in a fragrance or flavour composition prepared for addition to a triglyceride or derivative.

The term triglyceride and derivative extends to direct derivatives of triglycerides and compositions containing these materials. Examples are mono- and di-glycerides, glycerol, long chain fatty acids and their salts.

A common method of counteracting malodours is to ameliorate their effects by 'odour masking', ie the addition of organoleptically acceptable materials which act to suppress sensorially the perception of malodorants. The method described here, on the other hand, uses reaction products of amines and aldehydes with the potential to chemically reduce the concentration of aldehydic malodorants by direct chemical trapping, with comcomitant release of desirable perfume/flavour aldehydes into the product over time. This represents, in effect, an exchange process replacing unwanted aldehydes with desirable aldehydes.

A key feature of the invention is the use of chemically reactive malodour counteractants which may be used in the presence of typical fragrance/flavour components, without gross distortion of the overall sensory characteristics of the fragrance/flavour in the end product.

The malodour counteractants claimed in this invention are compatible with fragrances and flavours, but have the potential to produce in situ agents with nucleophilic centres which can react readily with compounds containing one or more aldehyde groups. An example of such an agent for a particular situation would be an amine with low odour impact and with good diffusive properties (to facilate permeation within a product). The amine could be generated within the product via, for example, an imino compound such as a Schiff's base. These materials are known to exist as equilibrium mixtures of the imine and the precursor compounds, the exact composition depending upon factors such as temperature, pH and amount of water present.

Whilst the precise mechanism of malodour reduction by the present invention is not known it is postulated that when a perfume or flavour incorporating a Schiff's base is added to a product the equilibrium position is likely to change, and re-equilibration occur, involving the undesired aldehydes present in the product. An exchange of aldehydes may therefore take place:

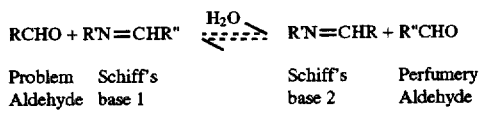

| Problem | Schiff's | Schiff's | Perfumery |
| Aldehyde | base 1 | base 2 | Aldehyde |

Schiff's base are known and utilised in perfumery, but differ from those described here in that they are generally prepared from amine precursors which are themselves known perfumery materials. Scission of such bases would therefore liberate amino-compounds with high odour impacts, with the potential to adversely affect the odour characteristics of the fragranced product.

However the use of the reaction products of amines and organoleptically acceptable aldehydes, usually referred to as Schiffs bases, to reduce the problem of the undesired aldehydic components in triglycerides and derivatives is a novel feature of the present invention.

Literature:

Attempts to reduce malodour using chemicals which react with malodorant materials are known. However the use of such materials with perfumes would be deleterious. Thus ozone (used in ventilator systems) would oxidise and destroy a large proportion of the terpenoids and unsaturated materials in perfumes. Sodium bisulphite (used in aqueous fish extracts J Food Sci., 48, 1064 to −1067, 1983) and alkanolamines per se (used in contaminated gas streams Pat. GB 1 596 752/3) would react with most aldehydes and would distort the odour characteristics of a typical perfume or flavour. Additionally, in the literature examples, it is the basicity of the alkanolamines which is exploited in order to reduce acidic malodours through simple acid-base reactions with carboxylic acids such as butyric and phenylacetic acids.

Amines are used to remove aldehydic impurities in a single component material, acrylic acid, (U.S. Pat. No. 3,725,208) but this is followed by a distillation stage to separate out the purified acid. Such a process is generally not suitable for the multi-component systems which are fragranced of flavoured.

Thus the chemicals used for odour removal in these examples are unsuitable for application in the presence of conventional fragrances or flavours.

Components of the invention:

Examples of the amine and aldehyde components usable in the invention are:

Amine Components i) Aminoalkanes of general formula:
  R $NH_2$ Where R is C1 to C16 alkyl, aryl or aralkyl ii) Diaminoalkanes of general formula:
  $H_2N(C_nH_{2n})NH_2$ Where ($C_nH_{2n}$) includes linear and branched chains and n is a maximum of 10 iii) Alkanolamines of general formula:
  $(NH_2)$ $(C_nH_{2n})(OH)$, where n is a maximum of 10, and their alkyl and (poly)oxyethylene ether derivatives.

For example, monoethanolamine (ie n is 2) $H_2NCH_2CH_2OH$ iii) Phosphatidylethanolamines of the type:

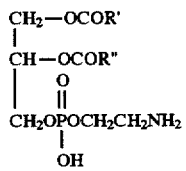

R', R" are each fatty acid alkyl residues containing at least 12 carbon atoms iv) Alpha-amino acid esters of the type:
  $H_2NCH(R")CO_2R'$
  R' is $CH_3$, Ph, $PHCH_2$, C2 to C4 straight and branched alkyl groups
  R" is H, $CH_3CH_2$, $CH_3CH_2CH(CH_3)$ $(CH_3)_2CHCH_2$, $H_2NCO$, $HSCH_2$ $RO_2CCH_2CH_2$, (where R=H,$CH_3$, $CH_3CH_2$), $CH_3SCH_2CH_2$, $HOCH_2$, $(CH_3)_2CH$, $PhCH_2$, P-hydroxyphenylmethyl For example:
  Leucine esters

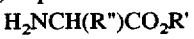

v) Beta-, or gamma-amino acid esters of general formula:
  $H_2N(CH_2)_nCO_2R$ n is 2 or 3 R is $CH_3$, Ph, Ph $CH_2$, C2 to C4 straight and branched alkyl groups.

These amines are organoleptically acceptable because the balance of the perfume is not disturbed.

Aldehydic Components:

i) Alkanals of types:
  a) $CH_3(CH_2)_nCHO$ where n is 0 to 14 and the chain may be straight, branched or cyclic.
  b) $CH_3(CH_2)_mCH(CH_3)(CH_2)_nCHO$ m+n is 0 to 8 ii) Unsaturated aldehydes of types:
  a) $CH_2=CH(CH_2)_nCHO$ where n is 6 to 9
  b) $CH_3(CH_2)_mCH=CH(CH_2)_nCHO$ m +n is 2 to 8
  c) Citronellal
  d) Phenylpropanals:
    R"$PhCH_2CH(R')CHO$ R' is H or $CH_3$ R" is H, isopropyl, tert-butyl
  e) Phenylacetaldehydes:
    PhCH(R)CHO R is H or $CH_3$
  f) Cyclohexene carboxaldehydes:

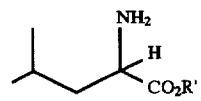

R', R", R" are each H or $CH_3$ g) Cinnamic aldehydes:
  PhCH=CH (R) CHO R=H, $CH_3$, pentyl, hexyl h) Benzaldehydes:
  RPhCHO R is H, isopropyl, $OCH_3$ or tertbutyl.

i) Hydroxy derivatives of a) to h), for example:
  Hydroxycitronellal

In the above lists of components Ph is either phenyl or phenylene.

Unsuitable amine components are i) esters of anthranilic acid in which the alkyl group of the ester is $CH_3$, $C_2$ to $C_4$ straight and branched chain alkyl groups, ii) o-aminoacetophenone. The amines are unsuitable because (i) and (ii) generally distort the perfume characteristics.

Specification description of the invention

Examples 1 and 2 describe the preparation and use of malodour counteractants based on ethanolamine and on leucine esters. Fragrances F1, F2 and F3 are floral soap perfumes available from Quest International UK Ltd.

EXAMPLE 1

A Schiff's base was prepared by adding undecanal dropwise over 1 hour to a stirred solution of 2-methoxyethylamine (equimolar) in ethanol (10% w/w) maintained at 4° to 5° C. The solvent was removed on a rotary evaporator to yield the expected Schiff's base (I) in 88% purity (by glc).

$$CH_3(CH_2)_9CH=N-(CH_2)_2OCH_3 \qquad (I)$$

This material was incorporated at several concentrations into soap perfume F1 which was used to fragrance soap derived from distilled fatty acids. This soap was known to contain unsaturated aldehydes, in particular 2,4-decadienal, by gc/ms analysis of the materials present in its headspace, ie air in contact with the soap. The odour character of the soap was distinctive, and its fatty, linseed-like notes were found to adversely affect perfume performance (for normal perfume loadings of 0.8% to 1.5% w/w).

Soap bars (ca 75 g) incorporating 1.2% by weight of perfume, with and without additive, were prepared by conventional milling, plodding and stamping. These bars were stored at 37° C. for 1 month prior to olfactory assessment by a sensory panel trained in the method of Magnitude Estimation (ME). The sensory results given in Table 1 suggest that perfume performance, as indicated by perceived perfume intensity, was enhanced in samples containing Product (I).

The observed improvement in perfume performance may be interpreted as arising from an effect on the malodour itself. Standard statistical tests (triangle tests) on samples of the perfume with/without product I showed that the presence of product I had no effect on the sensory characteristics of the fragrance.

TABLE 1

Perceived Perfume Intensities (ME) of Soap Bars Incorporating Perfume F1 with and without Product (I)

| % Product (I)* | Perceived Perfume Intensity** |
|---|---|
| 0 | 37.7 |
| 0.25 | 39.5 |
| 0.50 | 41.1 |
| 1.00 | 53.3 |

*w/w Relative to the perfume
**Arbitrary units (magnitude estimates)

EXAMPLE 2

Product (II) was prepared from an equimolar mixture of leucine ethyl ester free base (6.5 g, obtained from the hydrochloride salt ex Sigma) and dodecanal, in toluene as solvent. Water was removed by azeotropic distillation and, on cooling, the mixture was washed successively with dilute acid, bicarbonate solution and finally brine. Removal of toluene gave 10.5 g of a yellow material, Product (II).

Soap bars were made up as in Example 1, but using perfume F1 or F2 with/without additive. For comparison, ethyl leucine free base was itself included as an additive in the test. Storage conditions were as above, but odour assessment was carried out by an expert panel.

The results in Table 2 show soap bars which contained perfume incorporating malodour counteractant Product II achieved lower scores than did other soap bars, ie were preferred on average. It is instructive to note soap bars containing leucine ethyl ester free base, which has the potential to scavenge aldehydes directly, in fact scored worse than the control bars (with unmodified perfume) in three out of four cases.

TABLE 2

Odour Assessments of DFA Soap Bars Incorporating Perfume with/without Malodour Counteractants.

| Perfume | Additive | % Additive | Rank Sum |
|---|---|---|---|
| F1 | None | 0.00 | 11 |
|  | LE | 0.50 | 8 |
|  | LE | 2.00 | 15 |
|  | Product II | 0.50 | 6 |
|  | Product II | 2.00 | 5 |
| F2 | None | 0.00 | 10 |
|  | LE | 0.50 | 14 |
|  | LE | 2.00 | 12 |
|  | Product II | 0.50 | 3 |
|  | Product II | 2.00 | 6 |

Notes:
a) LE is leucine ethyl ester (free base)
b) % Additive is relative to perfume
C) Rank sum—obtained from two perfumers and one fragrance evaluator using a scale 1=best to 5=worst.

EXAMPLE 3

Materials used in this example were:

Flavour: coconut-flavour composition taken from the "Source Book of Flavours", AVI Publishers (1981), flavour code MF89 page 731

Malodour: 2, 4-dodecadienal

Counteractants:

a) 2-methoxyethylamine/undecanal reaction product (I)

b) Leucine ethyl ester/dodecanal reaction product (II)

The dienal was added (0.5%) to the coconut flavour composition (0.5%) to distort its flavour character with an off-note typical of degraded fats. The effectiveness of additives (I) and (II) in reducing the perceived intensity of the off-note, and restoring the original coconut character was then assessed sensorially for two systems dosed with 750 ppm of the flavour ie an oil in water emulsion, and a liqueur-type alcoholic solution.

After storage for one week the flavour with/without additives was taken up in the emulsion (prepared from ICI Speciality Chemicals HLB 10 mixture, at 10%, and Huile d'Avocat at 2%), and compared olfactorially with a standard (the untainted flavour) using an ordinal scaling technique. A similar experiment was carried out using the liqueur samples (made up with 25% alcohol and 23% sucrose).

The sensory results obtained from 10 panellists are summarised in Table 3.

TABLE 3

Olfactory assessment of liquids incorporating a tainted coconut flavour.

| Sample* | Average Score** | |
|---|---|---|
| | EMULSION | ALCOHOLIC SOLN. |
| Flavour + dienal | 2.65 | 2.7 |
| Flavour + dienal + (I) at 1% | 1.9 | 1.0 |
| Flavour + dienal + (II) at 1% | 1.45 | 2.3 |

*dienal incorporated into the flavour at 0.5%
**10 panellists, using a scale
1 = best (most true to original flavour)
3 = worst Samples containing products (I) and (II) achieved better scores than the tainted sample of the oil-in-water emulsion suggesting, that aldehydic malodour has been reduced. Trials using the additives in the absence of dienal did not reveal any significant differences between samples.

In the case of the alcoholic solutions the aldehydic malodour was much more prominent and a marked odour improvement was observed for samples incorporating additive (I).

EXAMPLE 4

Product (III) was prepared from the aldehyde 3-(4-tert. butylphenyl)-2-methylpropanal and 2-aminoethanol as follows:

The aldehyde (50 ml) was placed in a round-bottomed flask and to it was added 2-aminoethanol (12.5 ml) in ca. 1 ml portions with stirring.

The samples were dehydrated with anhydrous sodium sulphate (excess relative to the amount of water produced) and finally filtered through phase separation filter paper before dilution and use.

GC/MS data indicatied that the major product of the reaction was an adduct of the aldehyde and the amine.

EXAMPLE 5

Product (IV) was prepared from the aldehyde 4-(4-methyl-4-hydroxypentyl)-3-cyclohexenecarboxaldehyde and 2-aminoethanol as follows:

The aldehyde (50 ml) was placed in a round-bottomed flask and to it was added 2-aminoethanol (12.7 ml) in ca. 1 ml portions with stirring.

Workup was as in Example 4. GC/MS data indicated that the major product of the reaction was an adduct of the aldehyde and the amine.

EXAMPLE 6

Product (V) was prepared from 3-(4-tert. butylphenyl)-2-methylpropanal and 1,2-diaminoethane as follows:

The aldehyde (10.2 g) was placed in a round-bottomed flask and to it was added 1,2-diaminoethane (1.43 g) with stirring.

The reaction product was filtered through phase separation paper and used without further treatment.

Spectroscopic date ($^{13}$C/$^1$H NMR) of the reaction product was consistent with a mixture of the imine (1.1 adduct), the diimine (amine: aldehyde 1:2 adduct) and excess aldehyde.

EXAMPLE 7

Products (III), (IV) and (V) were incorporated separately into perfume F3 at a level of 0.5% w/w. Soap bars fragranced with F3 or its modifications were made up as described in Example 1, but using a standard high quality super-fatted soap base which had previously been dosed with 2,4-decadienal (a malodorant aldehyde) at a concentration of 50 ppm.

Following storage at 37° C. for 10 days, the soap bars were evaluated for olfactory performance by a panel of experts.

The sensory results given in Table 4 show that the bars containg perfumes incorporating the malodour counteractants achieved better scores than those containing the unmodified perfume.

TABLE 4

Odour Assessments of Malodorous Soap Bars incorporating Perfume with/without Malodour Counteractants.

| Perfume | Counteractant | % Counteractant | Rank Sum |
|---|---|---|---|
| F3 | None | 0.00 | 16.0 |
| | Product (III) | 0.50 | 11.0 |
| | Product (IV) | 0.50 | 7.0 |
| | Product (V) | 0.50 | 6.0 |

Notes:
a) % Counteractant is w/w relative to the perfume
b) Rank sums were obtained from 4 assessors using a scale 1 = best to 4 = worst.

We claim:

1. Perfumes and flavors comprising a reaction product of an organoleptically acceptable aldehyde and an amine which does not distort the sensory characteristics of the perfumes and flavors, wherein the aldehyde is chosen from:

i) Alkanals of types:

a) $CH_3(CH_2)_nCHO$ where n is 0 to 14 and the chain may be straight, branched or cyclic b) $CH_3(CH_2CH_3(CH_2)_n CHO$ m+n is 0 to 8 ii) Unsaturated aldehydes of types:

a) $CH_2=CH(CH_2)_nCHO$ where n is 6 to 9 b) $CH_3(CH_2)_mCH=CH(CH_2)_nCHO$ m+n is 2 to 8 c) Citronellal d) Phenylpropanals: R"PhCH$_2$CH(R')CHO R'is H or CH$_3$ R"is H. isopropyl, tert-butyl e) Phenylacetaldehydes: PhCH(R) CHO R is H or CH$_3$ f) Cyclohexene carboxaldehydes:

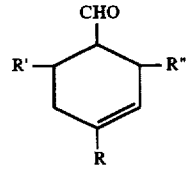

R, R', R" are each H or CH$_3$ g) Cinnamic aldehydes: PhCH=CH(R)CHO R=H CH$_3$, pentyl, hexyl h) Benzaldehydes: RPhCHO R is H, isopropyl, OCH$_3$ or tertbutyl i) Hydroxy derivatives of a) to h);

and the amine is chosen from:

i) Aminoalkanes of general formula:

R NH$_2$ Where R is [Cl] C$_1$ to C$_{16}$ alkyl, aryl or aralkyl, ii) Diaminoalkanes of general formula:

H$_2$N (C$_{11}$H$_{20}$) NH$_2$ Where (C$_8$H$_{20}$) includes linear and branched chains and n is a maximum of 10.

iii) Alkanolamines of general formula:

(NH$_2$) (C$_n$H$_{2n}$) (OH), where n is a maximum of 10, and their alkyl and (poly)oxyethylene ether derivatives.

Phosphatidylethanolamines of the type:

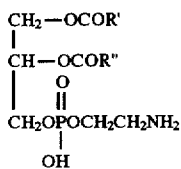

R', R" are each fatty acid alkyl residues containing at least 12 carbon atoms.

iv) Alpha-amino acid esters of the type:

H$_2$NCH(R") CO2R'

R' is CH$_3$, Ph, PhCH$_2$, C$_2$ to C$_4$ straight and branched alkyl groups.

R" is H, CH$_3$CH$_2$, CH$_3$CH$_2$CH(CH$_3$), (CH$_3$)$_2$CHCH$_2$, H$_2$NCO, HSCH$_2$, RO$_2$CCH$_2$CH$_2$, CH$_3$SCH$_2$CH$_2$, HOCH$_2$, (CH$_3$)$_2$CH, PhCH$_2$, p-hydroxyphenylmethyl.

v) Beta-, or gamma-amino acid esters of general formula:

H$_2$N(CH$_2$)$_n$CO$_2$R n is 2 or 3, R is CH$_3$, Ph, PhCH$_2$, C$_2$ to C$_4$ straight and branched alkyl groups.

* * * * *